(12) United States Patent
Oschman et al.

(10) Patent No.: US 6,695,761 B2
(45) Date of Patent: Feb. 24, 2004

(54) APPARATUS FOR ASSISTING A HEART

(75) Inventors: James L. Oschman, Dover, NH (US); Robert W. Gray, Rochester, NY (US)

(73) Assignee: Biomed Solutions, LLC, West Henrietta, NY (US)

( * ) Notice: Subject to any disclaimer, the term of this patent is extended or adjusted under 35 U.S.C. 154(b) by 200 days.

(21) Appl. No.: 10/060,516

(22) Filed: Jan. 30, 2002

(65) Prior Publication Data

US 2003/0144572 A1 Jul. 31, 2003

(51) Int. Cl.[7] ............................................. A61N 1/362
(52) U.S. Cl. .................................................. 600/16
(58) Field of Search .................. 607/1–114; 600/16–18

(56) References Cited

U.S. PATENT DOCUMENTS

2003/0060863 A1 * 3/2003 Dobak, III
2003/0088299 A1 * 5/2003 Magers et al.

* cited by examiner

Primary Examiner—Scott M. Getzow
(74) Attorney, Agent, or Firm—Howard J. Greenwald

(57) ABSTRACT

An implantable apparatus for treating a heart of a living organism which contains a device for withdrawing blood from the heart, for imparting helical flow to the blood, for recording at least one energy characteristic of the heart, and for imparting energy to the living organism.

20 Claims, 12 Drawing Sheets

APPARATUS FOR ASSISTING A HEART

FIELD OF THE INVENTION

An artificial heart device which contains fluted flow chambers, a heater, and devices for producing sound waves, electromagnetic radiation, pressure pulses, and magnetic lines of flux.

BACKGROUND OF THE INVENTION

Mechanical pumps and other circulatory support devices are being developed and utilized to replace or augment biological hearts in animals and humans. These devices are intended to replace or support damaged or diseased hearts and have proven capable of sustaining experimental animals and humans for various periods.

Various parameters of blood flow and heart action are important to long-term patient survival. For example, the heart produces a pulsing biomagnetic field in the space around the body that can be measured by the magnetocardiogram. While these pulsing biomagnetic fields are being increasingly utilized for diagnostic purposes, these fields also have physiological significance for the functioning of the organism as a whole.

It is known that natural hearts produce a variety of energetic pulsations. Some of these, such as the sound, electrical, and pressure pulses, measured respectively with the stethoscope or phonocardiogrph, electrocardiogram, and various pressure recording devices (manometers, kymograms, ballistocardiograms), are well understood and widely utilized as diagnostic indicators of heart and circulatory health. Less well known is the thermal or heat pulse produced by each contraction of the heart muscle.

Likewise, the pumping of the blood sets up important neural signals because of the operation of the aortic and carotid baroreceptor system.

While the focus of medical research and clinical practice has been on the utility of the various pulsations as diagnostic indicators, little attention has been given to the possibility that such energetic pulsations, electromagnetic, acoustic, photonic, thermal, mechanical, and so on, serve functional purposes in the overall economy and integration of organismal functioning. For example, a theory about the possible roles of the various energetic pulsations is disclosed in an article published in 1996 by L. G. Russek and G. E. Schwartz with the title "Energy Cardiology: A Dynamical Energy Systems Approach for Integrating Conventional and Alternative Medicine" published in "Advances: The Journal of Mind-Body Health," in Volume 12 on pages 4–24. Russek and Schwartz refer to the circulatory system and the blood flowing through it as a "dynamical energy system" that communicates information throughout the body, to every cell, integrating a variety of system-wide processes. Implicit in this model is the role of the blood as a systemic communication system by virtue of its high conductivity for electrical, mechanical, acoustic, and other energetic pulsations. Hence the vibratory properties of the circulation are conceived by Russek and Schwartz to form a dynamical system with a variety of regulatory roles. Research by others, to be cited below, supports this view.

It is recognized that complications associated with cardiac assist and replacement devices are multifaceted, and include multisystem organ failure, as is disclosed in a book edited by E Braunwald, D P Zipes and P Libby with the title "Heart Disease, A textbook of cardiovascular medicine" 6th edition, published by W B Saunders Company in Philadelphia on page 609 of Volume I. The prevalence of systemic complications following implantation of partial or total artificial heart devices is indicative of deficiencies that need to be overcome.

Systemic complications from the use of artificial hearts are also supportive of the dynamical energy theory developed by Russek and Schwartz and referenced above. Specifically, the Russek and Schwartz theory has implications for heart replacement therapies because it points toward the heart as a fundamental dynamic synchronizer producing rhythmic information that affects diverse systems. Failures of artificial cardiac support systems to maintain life for extended periods may be a reflection of disturbances in the cardiac coordination system postulated by Russek and Schwartz.

These concepts and observations also have implications for the patient with a weakened or damaged or diseased heart. Heart failure, for example, has a variety of systemic consequences, some of which obviously arise from decreased perfusion of various organs and tissues, and some of which may arise from changes in other physical characteristics of the blood flow addressed by this patent.

Understanding of the significance of the electrical signals generated by the heart has been expanded by recent discoveries concerning the frequency spectrum of the electrocardiogram and the corresponding biomagnetic spectrum as recorded with the magnetocardiogram. This information is cited here because an implanted artificial heart will obviously not produce an electrocardiogram or magnetocardiogram of a healthy, natural heart, and will be deficient in other energetic pulsations and rhythms as mentioned above, and these deficiencies could have local and systemic implications and affect long term patient survival.

Specifically, heart rate variability, measured with the electrocardiogram, can be converted mathematically into power spectral density, a widely used non-invasive clinical test of integrated neurocardiac functioning, as disclosed by Z Ori, G Monir, J Weiss, X Sayhouni and D H Singer in an article published in 1992 with the title, "Heart rate variability: Frequency domain analysis" published in Cardiology Clinics Volume 10 Number 3 on pages 499–537. These authors disclosed that heart rate variability distinguishes between sympathetic and parasympathetic regulation of the SA node. Subsequent research showed that heart rate variability is a predictor of a wide range of parameters, including mortality following myocardial infarction (as disclosed by R E Kleiger and J P Miller in 1978 in an article entitled "Decreased heart rate variability and its association with increased mortality after acute myocardial infarction" published in the American Journal of Cardiology Volume 59, pages 256–262, as well as in a 1998 paper by M T La Rovere, J T Bigger F I Marcus, A Mortara, P J Schwartz and ATRAMI Investigators entitled "Baroreflex sensitivity and heart-rate variability in prediction of total cardiac mortality after myocardial infarction" published in Lancet Volume 351, Number 9101 on pages 478–484), congestive heart failure (as disclosed in an article by P Saul, Y Arai, R Berger, L Lilly, W Colucci, and R Cohen published in 1988 with the title "Assessment of autonomic regulation in congestive heart failure by heart rate spectral analysis" published in the American Journal of Cardiology Volume 61 on pages 1292–1299), and coronary angiography (as disclosed by M W Saini et al. in 1988 in an article entitled "Correlation of heart rate variability with clinical and angiographic variables and late mortality after coronary angiography" published in the American Journal of Cardiology Volume 62 on pages 714–717). Heart rate variability is also predictive of rejection risk following transplantation (as disclosed by T Binder, B Frey, G Porenta, G Heinz, M Wutte, G Kreiner, H Gossinger, H Schmidinger, R Pacher, and H Weber in 1992 in an article entitled "Prognostic valve of heart rate variability in patients awaiting cardiac transplantation" published in Pacing and Clinical Electrophysiology Volume 15 on pages 2215–2220), it characterizes psychological illnesses including major depression (disclosed in 1991 by V. K. Yeragani et al. "Heart rate variability in patients with major depression" published in Psychiatric Research Volume 37 on pages 35–46) and panic disorders (as disclosed in an article by V K Yeragani, R Pohl, R Berger, R Balon, C Ramesh, D Glitz, K Srinivasan and P Weinberg entitled "Decreased HRV in panic disorder patients: a study of power-spectral analysis of heart rate" published in Psychiatric Research Volume 46 on pages 89–13), autonomic changes associated with hostility (as disclosed by R P Sloan, P A Shapiro, J T Bigger, E Bagiella, R C Steinman, and J M Gorman in an article published in 1994 with the title "Cardiac autonomic control and hostility in healthy subjects" published in the American Journal of Cardiology Volume 74 on pages 298–300), and risk from hypertension (as disclosed in a 1993 article by J H Markovitz, K A Matthews, W B Kannel, and J L Cobb entitled "Psychological predictors of hypertension in the Framingham study: is there tension in hypertension?" published in the Journal of the American Medical Association Volume 270 Number 20 on pages 2439–2494).

The implication of these findings is that a normal electrocardiogram, providing normal rate variability and normal electrocardiographic signatures, as well as providing normal energetic pulsations of other kinds mentioned above, can be correlated with a wide range of important systemic physiological and emotional attributes.

Additional extensive research on heart rate variability, its physiological and pathophysiological interpretations, and clinical applications will be found in a book with 66 contributing authors edited by M Malik and A J Camm published in 1995 with the title "Heart Rate Variability" and published by Futura Publishing Company. Also see a book edited by M. Di Rienzo, et. al. published in 1999 with the title, "Methodology and clinical applications of blood pressure and heart rate analysis" published in Amsterdam by IOS press. See also the book by R Takalo entitled "Variability of Blood Pressure and Heart Rate in Borderline and Mild Hypertension: With Special Reference to Spectral Analysis" published by Uppsala Universitet, 1999.

In 1995, R McCraty, M Atkinson, W A Tiller, G Rein and A D Watkins disclosed relationships between emotional state and the power spectrum of the heart rate variability, as described in an article entitled "The effects of emotions on short-term power spectrum analysis of heart rate variability" published in The American Journal of Cardiology in Volume 76, Number 14, on pages 1089–1093. Regular variations in heart rate and electrocardiographic recordings are correlated with a whole-body state referred to as "coherence," a state reflecting a balance between the rhythms of the sympathetic and parasympathetic branches of the autonomic nervous system that regulate the heart rate. This beneficial balanced state is associated with a coupling, or entrainment, or phase-locking of a variety of electrical and mechanical rhythms, including the heart, respiration, autonomics, and the baroreceptor feedback loop to the brain. The studies implicate the heart electricity, as measured by the electrocardiogram, as a systemic synchronizer of these various rhythmic processes.

Moreover, the heart generates the largest pulsing biomagnetic field of the body, which can be detected in the space around the body with a coil and/or with a superconducting quantum interference device (SQUID) as disclosed by D Cohen in 1967 in an article entitled "Magnetic fields around the torso: production by electrical activity of the human heart" published in Science Volume 156, pages 652–654, and also disclosed by D Cohen, E A Edelsack and J E Zimmerman in 1970 in an article entitled "Magnetocardiograms taken inside a shielded room with a superconducting point-contact magnetometer" published in Applied Physics Letters Volume 16, pages 278–280. This discovery is important because there is evidence that cellular regulations and healing processes in general can be influenced by low frequency pulsing electromagnetic fields as disclosed by B F Sisken and J Walker in 1995 in an article entitled "Therapeutic aspects of electromagnetic fields for soft-tissue healing" published in a book edited by M Blank entitled "Electromagnetic fields: biological interactions and mechanisms" published in Advances in Chemistry Series 250, American Chemical Society, Washington, D.C., on pages 277–285, and in an article by C A L. Bassett published in 1995 with the title "Bioelectromagnetics in the service of medicine" published in a book edited by M Blank with the title "Electromagnetic fields: biological interactions and mechanisms" published in Advances in Chemistry Series 250, American Chemical Society, Washington, D.C. on pages 261–275.

Some have argued that the energy contained in the electrocardiograms and magnetoencephalograms must be far too weak relative to ambient and internal noise to produce significant physiological or emotional effects on cells and tissues and organs a distance away from the source. However, recent research has shown that the noise in a biological system can play a constructive role in the detection and utilization of weak rhythmic signals by a nonlinear cooperative effect known as stochastic resonance. In essence, a regular periodic signal can entrain ambient noise to boost the signal to a level above the threshold value, enabling it to generate measurable effects on cellular activities. Stochastic resonance has been firmly established as a valid phenomenon in a wide range of sensory and neural systems and is being exploited in electronic equipment, as disclosed by K Wiesenfeld and F Moss in 1995 in an article entitled "Stochastic resonance and the benefits of noise: from ice ages to crayfish and SQUIDs" published in Nature, Volume 373, pages 33–36 and in an article by A R Bulsara and L Gammaitoni in 1996 with the title "Tuning into noise" published in Physics Today, March issue, pages 39–45. All of these concepts strengthen our assertion that the various energetic pulsations produced by the biological heart can have constructive effects throughout the body, and that their absence in the patient with an implanted artificial heart can have deleterious consequences.

Another attribute of blood flow is its rheological characteristics, which will obviously not be the same for an artificial mechanical heart compared with a biological heart. The importance of mechanical impulses in cardiac assist devices is documented in a paper by S M Mehta, T X Aufiero, W E Pae Jr et al, 1996, entitled "Results of mechanical ventricular assistance for the treatment of post cardiotomy cardiogenic shock" published in American Society for Artificial Internal Organs Journal Volume 42, p. 211. These authors found that postimplant hemorrhage occurs more frequently in patients supported with a ventricular assist device with a centrifugal pump than in patients supported with a pulsatile pumping device for the same indication, postcardiotomy cardiogenic shock.

Pulsatile and nonpulsatile blood flow have been compared by A Ündar, N Henderson, G B Thurston, T Masai, E A Beyer, O H Frazier, and C D Fraser Jr. in a 1999 report in an article with the title "The effects of pulsatile versus nonpulsatile perfusion on blood viscoelasticity before and after deep hypothermic circulatory arrest in a neonatal piglet model" published in Artificial Organs Volume 23 Number 8, pages 717–721. These authors found that the pulsatile pump system produces less blood trauma than the standard non-pulsatile roller pump as indicated by lower values of both viscosity and elasticity during cardiopulmonary bypass. Blood trauma increases blood viscoelasticity by increasing red cell aggregation and plasma viscosity and by decreasing cell deformability.

There has been debate over the effectiveness of pulsatile versus nonpulsatile perfusion, but there are clear physiological benefits of pulsatile perfusion during cardiopulmonary bypass compared to nonpulsatile perfusion, as disclosed by A Undar, A J Lodge, C W Daggett, T M Runge, R M Ungerleider, and J H Calhoon in 1998 in an article entitled "The type of aortic cannula and membrane oxygenator affect the pulsatile waveform morphology produced by a neonate-infant cardiopulmonary bypass system in vivo" published in Artificial Organs Volume 22 number 8 on pages 681–686.

In 1932, J. Bremer described the "presence and influence of spiral streams in the heart of the chick embryo" in an article published in the American Journal of Anatomy in Volume 49, on pages 409–440. Bremer disclosed that, in the chick embryo of about forty-hours and older, "the two streams, definitely right and left as they flow down the atrioventricular canal, can be followed through the ventricles." Bremer also listed earlier authors who had noted this phenomenon.

In 1973, D E M Taylor and J D Wade disclosed the results of cineradiography with fine stream dye injection, in an article entitled "Pattern of blood flow within the heart: a stable system" published in Cardiovascular Research, Volume 7, pages 14–21. They noted that the flow patterns within the cardiac ventricles during diastolic filling in dogs and sheep are expanding vortex systems behind the cusps of the mitral and tricuspid valves.

In 1981, B L Langille and S L Adamson authored a paper entitled "Relationship between blood flow direction and endothelial cell orientation at arterial branch sites in rabbits and mice" that was published in Circulation Research in Volume 48 on pages 481–488. In this paper the authors disclosed that the patterns of orientation of endothelial cells near arterial branch sites were almost identical to the orientation of the flow streamlines near the vessel walls. In their article, Langille and Adamson summarized the work of others indicating that flow-induced alterations in endothelial cells may be a factor in atherosclerosis. They also summarized research of others indicating that the shape and orientation of endothelial cells is determined by blood flow characteristics.

In 1983, B. S. Massey disclosed that counter-rotating helices tend to develop at simple pipe bends, in his book entitled, "Mechanics of fluids" published by Van Nostrand Reinhold in the United Kingdom, on pages 222–224.

In 1984, Y. C. Fung disclosed that the heart is twisted on its axis and the aortic arch is tapered, curved, and twisted, in his book entitled "Biodynamics: circulation", published by Springer-Verlag, on pages 77–164.

In 1991, P A Stonebridge and C M Brophy disclosed that fiber-optic angioscopic examination shows "that the inner surface of blood vessels is often not smooth but organized in a series of spiral folds" in their article entitled "Spiral laminar flow in arteries?" published in The Lancet in Volume 338 on pages 1360–1361. These authors described a number of observations indicating that "spiral blood flow is a normal process, at least in parts of the circulation."

Kilner et al, 1993 disclose the "Helical and retrograde secondary flow patterns in the aortic arch studied by three-directional magnetic resonance velocity mapping" published in Circulation in Volume 88 (part 1) on pages 2235–2247. Right-handed helical flows predominate in the upper aortic arch in late systole, with end-systolic retrograde flow along inner wall curvatures. These consistent features of intra-aortic flow in healthy subjects arose, in part, from the curvature of the arch and the pulsatility of flow in it.

Finally, rhythmic operation of the baroreflex system has implications for systemic circulation via the vasomotor center in the medulla, which regulates heart rate and vasodilation/vasoconstriction throughout the body. Obviously a nonpulsatile cardiac assist device or artificial heart or a failing heart will not provide the rapid rhythmic pulsations in blood pressure and consequent neural impulses in nerves ascending from the aortic and carotid baroreceptors, and this will have systemic consequences. Moreover, there is evidence that the timing of the baroreflex pulsations in relation to the cardiac and respiratory rhythms has systemic physiological and emotional effects, and the present invention acknowledges these relationships by including means for optimizing them.

Extensive research and prior art relates to cardiac assist devices, artificial hearts, artificial prosthetic conduits, and artificial or replacement valves for such devices. Additional art relates to rhythmic processes, their relationships, and the therapeutic significance of appropriate rhythmic timing.

Key to the deployment of long-term implantable cardiac devices is the development of bio-compatible materials and conduits that do not allow for the formation of blood stagnation or stasis volumes or sites for bacterial growth and infection that are hidden from the patient's immune system and that do not introduce or allow the entry of bacterial or other contamination into the patient's body or circulatory system. This biocompatible materials should have a minimum of blood-contacting material-surface transitions that can become misaligned and thereby introduce turbulence to the flow, but should not have differing degrees of surface properties that provide an opportunity for biological interfaces forming on such surfaces clot or to slough off to become emboli in the circulating blood. The bio-compatible materials should also provide for changing dimensions of conduits as blood pulses through them or as materials change dimensions over weeks or months after implantation into the body.

Thus, U.S. Pat. No. 5,810,708 ("Ventricular assist conduit with externally supported tissue valve") discloses "a valved blood conduit having woven and/or knitted filamentary fabric walls which are impregnated outwardly with a biologically-compatible impermeable material so that the conduit walls are impermeable to blood, while the inner surface of the conduit wall remains textured or porous to promote the growth of a stable biological interface. Provision is made for sealingly connecting the valved blood conduit to other blood-carrying components without disruption of smooth and stasis-free blood flow. The connecting provisions also minimize the number of blood-contacting material-surface transitions, and provide for accommodation without loss of sealing integrity of dimensional changes which will occur at the connections after implantation of the valved conduit and assist device. These dimensional changes will occur as a transitional collagen or other biodegradable coating of the conduit is absorbed, as components of the valved conduit and adjacent structure take a set with the passage of time after surgical implantation, and as a biological interface is formed on the blood-contacting surfaces by the host's circulatory system." The wall of the conduit is preferably composed of "a single ply of tubular-woven and/or knitted polyethylene terephthalate fabric . . . transfer-coated externally with sheet silicone rubber material . . . so that it forms a liquid-impermeable barrier or membrane integral with the fabric . . . producing a porous inner surface into which a stable biological interface may implant." The result is a conduit with a single unitary blood-contacting flexible wall without the use of gaskets or other sealing devices which are exposed to the flowing blood. The entire disclosure of this United States patent application is hereby incorporated by reference into this specification.

Incorporation of valves in a blood conduit requires consideration of prior art relating to artificial prostheses as substitutes for valves in the human heart. U.S. Pat. No. 6,228,112, "Artificial heart valve without a hinge," discloses prior art valves which, by their construction and design, impede blood flow and can create stagnation that can lead to thrombosis, and which, in some cases, have hinges that can malfunction. The invention described in U.S. Pat. No. 6,228, 112 overcomes these prior art limitations with a valve structure without hinges. The entire disclosure of this United States patent is hereby incorporated by reference into this specification.

Of particular importance when considering valvular structures in the circulation is the problem of wear. Worn out valves present hazards to the patient, not the least of which is the higher operative mortality rate associated with second and third reoperations to replace worn out valves. While artificial materials can be manufactured into valves that do not wear out and consequently do not require replacement, bioprosthetic or tissue valves are often preferred because of their better biocompatibility. Blood can adhere and clot on mechanical valves, requiring that the patient be continually treated with anticoagulants. However, these treatments have risks of their own, including bleeding and thromboembolism. These drawbacks and other problems with the prior art are discussed and resolved in U.S. patent application Ser. No. 20010002445 "Bioprosthetic cardiovascular system," which teaches a method of building valves that can be routinely removed when they begin to fail and then replaced using catheter-based endovascular procedures or minimally invasive surgery, with low attendant morbidity. The patent application teaches a valve design that is sufficiently collapsible so as to be able to be passed through the lumen of a catheter inserted into the femoral artery or other large vessel. The collapsed valve is re-expanded to fit into a permanent housing or base unit installed in the patient's heart. The valve can be collapsed again for removal once the valve wears out. While a variety of materials are available, the cited invention utilizes valve leaflets constructed from sheets of chemically preserved bovine pericardium. The entire disclosure of this United States patent application is hereby incorporated by reference into this specification.

The optimal timing of the various rhythmic process in relation to one another (heart, respiration, baroreflexes) is the subject of considerable research and prior art. Thus, U.S. Pat. No. 5,997,482, entitled "Therapeutic method for a human subject" discloses "a therapeutic method for a human subject which determines an optimal relationship between respiratory frequency and heartbeat unique for any given patient by utilizing Fourier analysis." In particular, U.S. Pat. No. 5,997,482 describes the benefits of high amplitude low-frequency harmonic oscillations in the heart rate, in the frequency range of 0.01–0.14 Hertz, that are "associated with a tendency to decrease psycho-emotional strain, reduced tiredness and reduced chronic agitation (see also a 1983 article by E. G. Vashillo et al entitled "Research of Resonance Characteristics of a Cardiovascular system" published in the U.S.S.R Academy volume 257). Within the specified frequency range, "every individual has a unique 'resonance' frequency which, when these oscillations reach their highest amplitude, the patient recognizes a general well being and improvement in a variety of therapeutic conditions." The therapeutic method employed in U.S. Pat. No. 5,997,482 involves registering a subject's current respiration rate and converting it into a first electrical signal, registering a current heartbeat of the subject and converting it into a second electrical signal, spectrally analyzing the first and second electrical signals to generate a resulting signal corresponding to a phase shift there between. In U.S. Pat. No. 5,997,482, biofeedback is used to maximize and maintain the ideal resonance relationships between rhythms, with a zero or minimum phase shift between the heart and breath oscillations. Positive impacts of maintaining these rhythmic relationships are: pulse rate decreases to an average 7–10 beats per minute among children and to 5–6 beats per minute among athletes, arterial pressure is normalized, the blood circulation in peripheral parts of the body improves, and the speed of voluntary muscle relaxation increases. The entire disclosure of each of these United States patents is hereby incorporated by reference into this specification.

The method of U.S. Pat. No. 5,997,482 has been used to treat bronchial asthma, neuroses, heart rate disorders, and disorders of the autonomic nervous system. The method is designed to decrease psychological tension. The method facilitates the well-researched phenomenon of the "relaxation response" with its plurality of physiological and psychological benefits.

Related art discusses the rhythms of the baroreflex arc, which are particularly relevant to heart failure. A patient's responses to this disorder are complex and include involvement of the sympathetic nervous system, the renin-angiotensin system, and other neuroendocrine systems, all affecting the peripheral vasculature. The baroreflex system provides partial control of the heart rate and peripheral vasculature. The baroreceptors in the aorta and carotid arteries respond to increases or decreases in arterial blood pressure by firing more or less frequently. Nerves transmit these impulses to the brain which modifies heart rate and vasomotor tone throughout the body and affects the sympathetic/parasympathetic balance. Modulation of baroreflex activity by electrical stimulation of carotid sinus nerves has been used to treat hypertension and intractable angina pectoris.

Carotid sinus nerve stimulation has been developed by Medtronic, Inc., of Minneapolis, Minn. In the 1960s to early 1970s, Medtronic produced and marketed two carotid sinus nerve stimulators for treatment of hypertension, the "Barostat," and angina, the "Angistat." These devices lowered blood pressure, decreased myocardial work and oxygen consumption, alleviating hypertension and angina. Moreover, ischemia detection has been used to regulate baroreflex nerve stimulation in an implanted device as described in the international publication WO92/16257.

More recently, U.S. Pat. No. 6,073,048, entitled "Baroreflex modulation with carotid sinus nerve stimulation for the treatment of heart failure," discloses a system and method for stimulating the baroreflex arc based on levels of indicators from the body, including heart activity and other indicators. This patent includes "a system for coordinating the stimulation of nerves for controlling the level of neurohormonal activation in a living body having a heart subject to potential or actual pathologic stress levels comprising: an implantable pulse generator with a microprocessor and memory adapted and disposed to run a plurality of processes, a sensor for sensing and measuring the value of an indicator of SVR (systemic vascular resistance) in the body, adapted and disposed to provide readings to said microprocessor for use by said processes, a bradycardia pacer control process included within said pulse generator for pacing the heart when a condition of bradycardia is present so as to prevent insufficient heart rate by said heart, at least one stimulation electrode connected to effectively deliver electrical stimulation output to a baroreceptor nerve site, a process for monitoring heart rate and estimating SVR from said sensor in order to modify said stimulation output, a system wherein said process for estimating SVR increases said stimulation output at a predetermined level of estimated SVR and decreases said stimulation output at another predetermined level of estimated SVR, a system further comprising an activity sensor, wherein said process for estimating SVR comprises a check of the activity sensor level made before increasing said stimulation output, a system further comprising an additional process within said pulse generator wherein if the estimated SVR is not determined to be above a predetermined level nor below another predetermined level, said additional process determines whether pacing is needed, and if so provides for a decreased amount of said stimulation output, a system wherein if said activity sensor indicates strenuous exercise, said stimulation output is suspended for the duration such indication is present, a system further comprising an intracardiac electrode and an additional process within said pulse generator, wherein said additional process provides that said stimulation output is gated to electrocardiographic indicators of cardiac activity received by said intracardiac electrode, a system wherein said additional process provides comprises variable stimulation output settings and delay timing, a method of automatically optimizing the cardiovascular responsiveness of a patient for the patient's condition through controlled application of electrical stimulation of nerves emanating from baroreceptors of said patient comprising: providing electrical stimulation to said nerves of sufficient intensity and duration so as to reduce neurohormonal activation and induce peripheral blood vessel dilation and a drop in heart rate, determining the responsiveness of the patient's body to said stimulation by sensing a feedback parameter of patient's responsiveness indicating altered cardiovascular function; and adjusting said electrical stimulation provided to the nerves based on said feedback and an optimization algorithm until the patient's cardiovascular system is optimized for his/her condition, sensing activity of said patient using an activity sensor, and if said activity sensor indicates periods of activity, suspending or lowering intensity of said electrical stimulation until a period of time after the sensed activity has ceased." The entire disclosure of this United States patent is hereby incorporated by reference into this specification.

U.S. Pat. No. 6,073,048 also discloses a method wherein, when an optimization algorithm is informed of overshoot in the drop in heart rate and/or peripheral vascular resistance, it responds by reducing the stimulation of the nerves arising from the baroreceptors; and, additionally, it also describes a method wherein, if overshoot of drop in heart rate passes a predetermined threshold, pacing the heart to maintain a predetermined heart rate. This patent also discloses a method of controlled application of electrical stimulation of nerves emanating from baroreceptors of said patient comprising: providing electrical stimulation to said nerves of sufficient intensity and duration so as to reduce neurohormonal activation and induce peripheral blood vessel dilation and a drop in heart rate, sensing activity of said patient using an activity sensor, and if said activity sensor indicates periods of activity, suspending or lowering intensity of said electrical stimulation until a period of time after the sensed activity has ceased. The process of this patent uses closed loop feedback techniques to improve baroreflex activity. It is potentially useful for patients with congestive heart failure including cases caused by coronary artery disease, myocardial infraction and chronic hypertension but not limited to these causes. The entire disclosure of this United States patent is hereby incorporated by reference into this specification.

U.S. Pat. No. 6,073,048 teaches that, in heart failure, inappropriate sympathetic nervous system activation causes vasoconstriction, neurohormonal stimulation, and increased systolic calcium. All of these factors contribute to a progression of the heart failure symptoms including cardiac arrhythmias and sudden death. Overdriving the central nervous system nerves with the invention of this patent can alleviate these factors. If the human sensor indicates stimulation is needed, stimulation commences and alleviates vasoconstriction which in turn decreases afterload, decreases myocardial energy expenditure, and prevents myocardial cell death. The stimulation also acts to decrease the prevalence of cardiac arrhythmias and to decrease cytosolic calcium levels, which in turn decreases chronotropy and inotropy, decreases cell energy expenditure and prevents cell death. Stimulation also decreases neurohormonal output which is inappropriately elevated in congestive heart failure and is associated with the reduction in cardiac output. The entire disclosure of this United States patent is hereby incorporated by reference into this specification.

It is an object of this invention to provide a device to record and store and restore or reintroduce to the blood flowing from an artificial heart or cardiac support device important pulsatile and flow characteristics that are absent when blood is caused to circulate by artificial means.

It is another object of this invention to provide a device for restoring certain physical characteristics of blood flow from a biological heart that has been compromised or weakened by damage or disease.

It is a further object of the invention is to provide a device adapted to reintroduce electromagnetic pulses to the blood emerging from artificial hearts or cardiac assist devices or to restore the strength and quality and timing of the electromagnetic pulses to blood emerging from a biological heart that has been compromised or weakened by damage or disease.

It is another object of the invention to provide a device adapted to reintroduce or strengthen the pattern of pulsing electromagnetic fields that a normal healthy heart radiates into the surrounding tissues and that gives rise to the normal electrocardiogram and magnetocardiogram.

It is yet another object of the invention to reintroduce acoustic pulses to the blood emerging from artificial hearts or cardiac assist devices or to restore the strength and quality of the acoustic pulses to blood emerging from a biological heart that has been compromised or weakened by damage or disease.

Another object of the invention is to provide an apparatus designed to reintroduce pressure pulses to the blood emerging from artificial hearts or cardiac assist devices or to restore the strength and quality of the pressure pulses to blood emerging from a biological heart that has been compromised or weakened by damage or disease.

A further object of the invention is to provide a device to reintroduce heat pulses to the blood emerging from artificial hearts or cardiac assist devices or to restore the strength and quality of the heat pulses to blood emerging from a biological heart that has been compromised or weakened by damage or disease.

Another object of the invention is to provide a device to reintroduce vortical or spiraling motions to the blood emerging from artificial hearts or cardiac assist devices that do not produce such flows or to restore the strength and quality of the vortical or spiraling motions to blood emerging from a biological heart that has been compromised or weakened by damage or disease.

Yet another object of the invention is to provide means for recording and storing various physical pulses produced during the operation of a healthy heart so said pulses can be recorded and reintroduced into a patient that is lacking or deficient in such pulsations for whatever reason.

SUMMARY OF THE INVENTION

In accordance with this invention, there is provided an implantable apparatus for treating a heart which is comprised a fluted flow chamber, means for recording the energy properties of a heart, means for imparting energy to the blood flowing through said heart wherein said energy is selected from the group consisting of thermal energy, acoustic energy, electromagnetic energy, magnetic energy, and mixtures thereof.

BRIEF DESCRIPTION OF THE DRAWINGS

The invention will be described by reference to the following drawings, in which like numerals refer to like elements, and in which.

DESCRIPTION OF THE PREFERRED EMBODIMENTS

Figure 1:
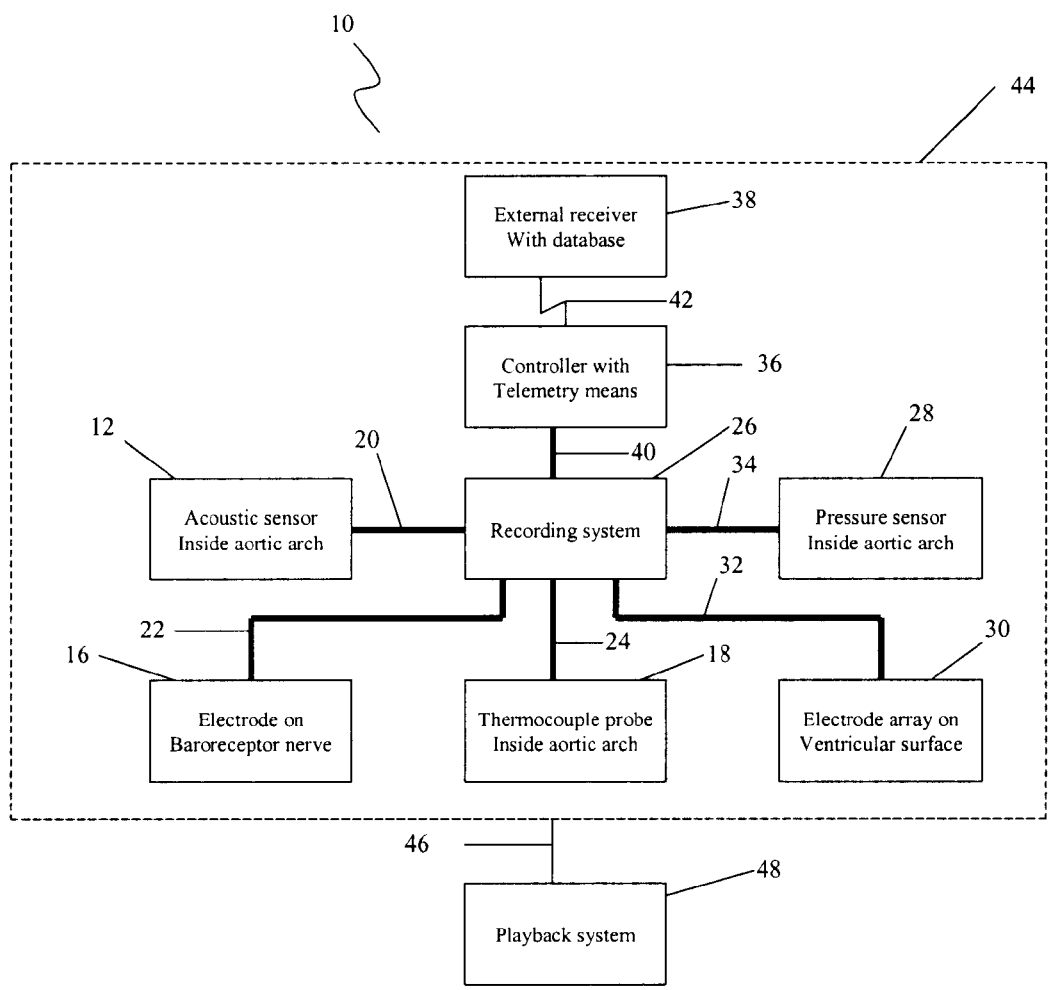
FIG. 1 is the schematic diagram of one of a preferred recording system.

FIG. 1 is a schematic diagram of one preferred recording apparatus 10 of the invention. This device 10 is adapted to record the various rhythms in an intact, healthy heart.

Referring to FIG. 1, it will be seen that device 10 is comprised of an acoustic sensor 12 which, in the preferred embodiment depicted, is disposed within the aortic arch 14 (see FIG. 2) of a human heart. These acoustic sensors are well known to those skilled in the art. Reference may be had, e.g., to U.S. Pat. No. 6,264,603 (Middle ear vibration sensor using multiple transducers), U.S. Pat. No. 6,093,144 (Implantable microphone having improved sensitivity and frequency response), and the like. The disclosure of each of these United States patents is hereby incorporated by reference into this specification.

Figure 2:
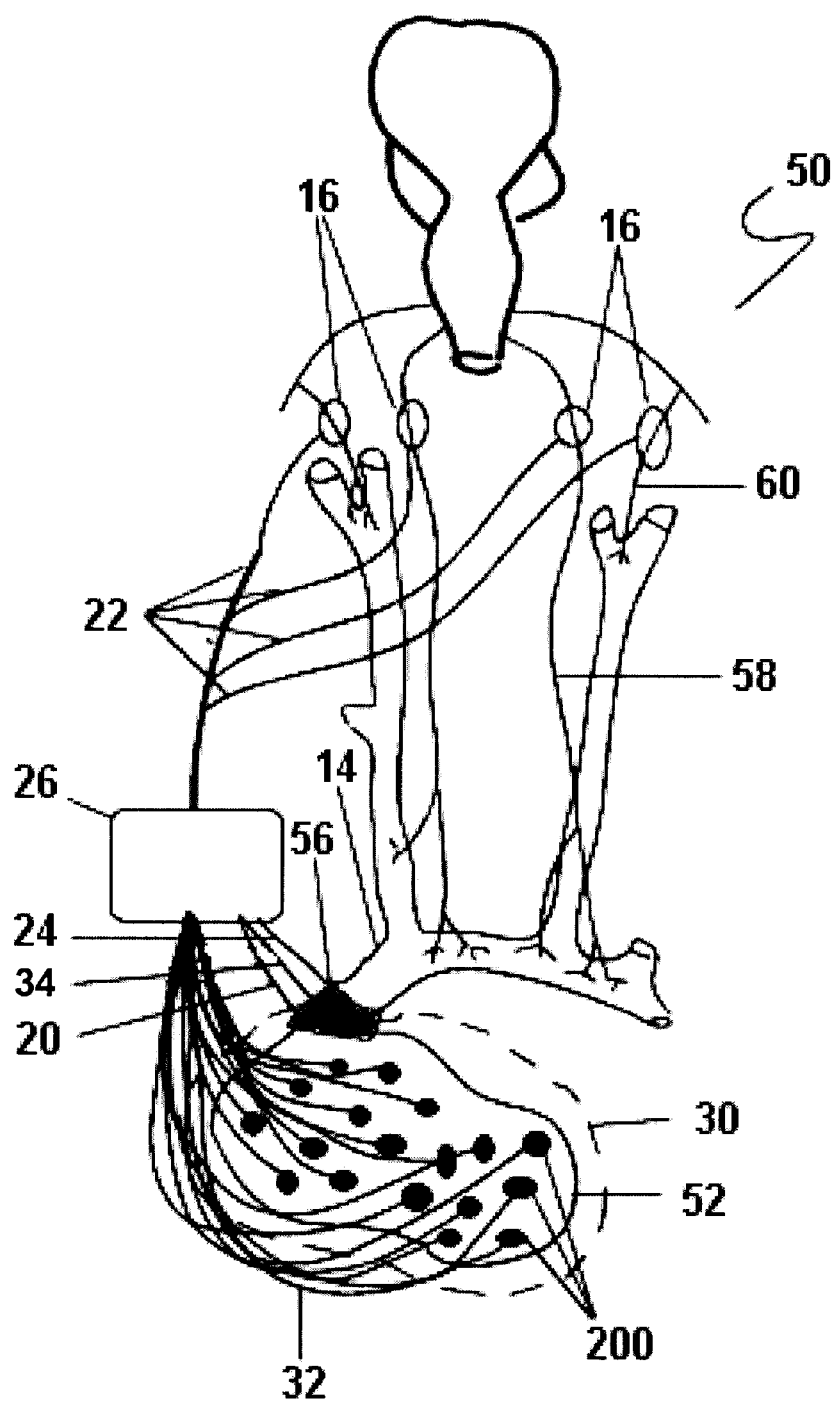
FIG. 2 illustrates the device of FIG. 1 connected to a human heart.

The acoustic sensor 12 is preferably disposed inside the aortic arch 14 (see FIG. 2). As is known to those skilled in the art, the aortic arch is that portion of the aorta extending from the heart to the third thoracic vertebra. Reference may be had, e.g., to U.S. Pat. Nos. 6,248,086, 6,132,397, 5,824,064, 6,099,548, 5,216,032, and the like. The entire disclosure of each of these United States patents is hereby incorporated by reference into this specification.

Referring again to FIG. 1, an electrode 16 records signals from one of the nerves in the baroreceptor system. As is known to those skilled in the art, the baroreceptor system is responsive to pressure. Reference may be had, e.g., to U.S. Pat. No. 4,791,931. The entire disclosure of this United States patent is hereby incorporated by reference into this specification.

A thermocouple probe 18 disposed within aortic arch 14 (see FIG. 2) measures the thermal transients within the aortic arch 14. One may use known implantable means for measuring temperature. Thus, e.g. one may use one or more of the temperature measuring devices disclosed in U.S. Pat. No. 5,564,434 (Implantable capacitive absolute pressure and temperature sensor), U.S. Pat. No. 6,254,548 (Internal thermometer) and the like. The entire disclosure of each of these United States patents is hereby incorporated by reference into this specification.

Referring again to FIG. 1, information from the acoustic sensor 12, electrode 16, and the thermocouple probe 18 is communicated via lines 20, 22, and 24, respectively, to recording system 26. Lines 20, 22, and 24, consist, e.g., of wires, fiber optics cables or other communication means. One may use conventional implantable recording systems for recording system 26. Reference may be had, e.g., to U.S. Pat. No. 5,776,168 (EGM recording system for implantable medical device), U.S. Pat. No. 5,970,986 (apparatus for rejection diagnostics after organ transplants), U.S. Pat. Nos. 5,832,488, 5,499,626, and the like. The entire disclosure of each of these United States patents is hereby incorporated by reference into this specification.

Referring again to FIG. 1, also disposed within the aortic arch 14 (see FIG. 2) is an implantable pressure sensor 28 which may be any of the prior art implantable pressure sensors. Thus, e.g., one may use one or more of the pressure sensors described in U.S. Pat. No. 6,221,024 (Implantable pressure sensor and method of fabrication), U.S. Pat. No. 5,013,396 (Method of making an ultraminiature pressure sensor), and the like. The entire disclosure of each of these United States patents is hereby incorporated by reference into this specification.

Referring again to FIG. 1, an electrode array 30 is preferably disposed over the ventricular surface 52 (see FIG. 2) of the heart. One may use conventional implantable electrode arrays such as, e.g. those disclosed in U.S. Pat. No. 6,205,361 (implantable expandable multi-contact electrodes), U.S. Pat. No. 6,171,239 (systems, methods, and devices for controlling external devices by signals derived directly from the nervous system), U.S. Pat. No. 6,141,591, (magnetless implantable stimulator), U.S. Pat. No. 6,119,044 (cochlear electrode array), U.S. Pat. No. 6,052,624 (implantable electrode arrays), U.S. Pat. No. 5,957,958 (implantable electrode arrays), U.S. Pat. No. 5,571,148 (implantable multi-channel stimulator), and the like. The entire disclosure of each of these United States patents is hereby incorporated by reference into this specification.

Information from the electrode array 30 is conveyed via lines 32 to recording system 26. Similarly, information from the pressure sensor 28 is conveyed to the recording system 26 via line 34.

Referring again to FIG. 1, and in the preferred embodiment depicted therein, a controller 36 with internal telemetric transceiver means (not shown) suitable for transmitting the recorded data in recorder 26 to an external receiver 38 is connected to recorder 26 via line 40. In another embodiment, not shown, the controller 36 may be connected to recorder 26 via telemetry means.

The controller 36 may use conventional implantable telemetric means 42 such as, e.g. a transceiver, a wire, a fiber optics connection, radio frequency transmitters, and the like to convey the collected data in recorder 26 to the external receiver with database 38. Such telemetric means are known to those skilled in the arts and are disclosed in U.S. Pat. No. 6,113,553 (Telemetric intracranial pressure monitoring system), U.S. Pat. No. 6,277,078 (System and method for monitoring a parameter associated with the performance of a heart), U.S. Pat. No. 5,016,634 (Implantable medical device with means for telemetric transmission of data), U.S. Pat. No. 5,413,594 (Method and apparatus for interrogating an implanted cardiac device), and the like. The entire disclosure of each of these United States patents is hereby incorporated by reference into this specification.

In the embodiment depicted in FIG. 1, an external receiver 38 is used to receive information from the controller 36. The external receiver preferably contains a database, and it may be computer controlled. Thus, e.g., one may use a computer-controlled receiver sold by the Icom Corporation as PCR-1000-02. Alternatively, or additionally, one may also use a comparable computer controlled transceiver. The computer circuitry can not only store information about selected frequencies and provide the reception and filtering means required, but it also can store information about a particular patient, his malady, his treatment history, etc.

Figure 5:
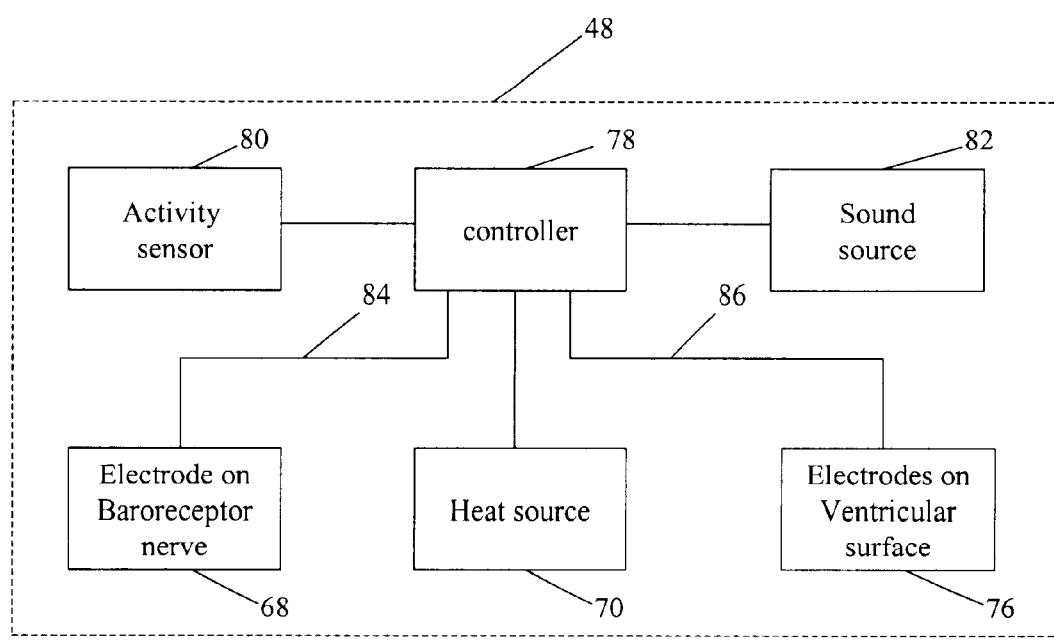
FIG. 5 is a schematic diagram of one embodiment of the heart augmentation device of this invention.

Referring again to FIG. 1, and in the embodiment depicted, elements 12, 16, 18, 30, 28, 26, 36, and 38 collectively comprise a preferred embodiment of a recording system 44. In the embodiment depicted, recording system 44 is operatively connected via line 46 to playback system 48. One preferred embodiment of playback system 48 is illustrated in FIG. 5 and will be described in more detail elsewhere in this specification.

FIG. 2 is a schematic representation of the components of recording system 44 within a patient 50. For the sake of simplicity of representation, only certain organs of patient 50 are depicted.

Referring to FIG. 2, it will be seen that, in the embodiment depicted, an electrode array 30 records the distribution of electrical fields over the ventricular surface 52. As will be apparent to those skilled in the art, every time the heart, which is a muscle, beats, electrical fields are generated. Thus, electrode array 30 is an indirect means of monitoring the activity of the heart.

A pressure sensor 28 (see FIG. 1) records pressure pulses inside the aortic arch 14. As will be apparent, the pressure within the aortic arch will vary with the cycle of the heartbeat.

A recording system 26 (see FIG. 1) stores the information from the various sensors. The various sensors utilized in this embodiment of the invention are well known to those experienced in the art; see, e.g., the patents cited elsewhere in this specification. By way of further illustration, in 1982 A. L. Wit et al. published an article on "Electrophysiologic mapping to determine the mechanism of experimental ventricular tachycardia initiated by premature impulses" in the American Journal of Cardiology Volume 49, pages 166–185; this article disclosed a placque electrode array used to map activation on the epicardial surface of the dog ventricle, said array bearing 384 unipolar electrodes at intervals of 2 millimeters.

Referring again to FIG. 2, there is shown a preferred deployment of the recording system 44 (illustrated in FIG. 1) with its plurality of sensors, including an array 30 of electrical sensors 200 distributed over the surface of the ventricle 52, and connected via lines 32 to the recording system 26, as well as acoustic 12, temperature 18, and pressure 28 sensors (see FIG. 4) located in a sensor cuff 56 placed around the proximal portion of the aortic arch 14, said sensors connected via lines 20, 24, 34 to the recording system 26, and electrodes 16 on afferent nerves 58 or 60 of the baroreceptor system, said electrode being connected via a lines 22 to the recording system 26.

Figure 3:
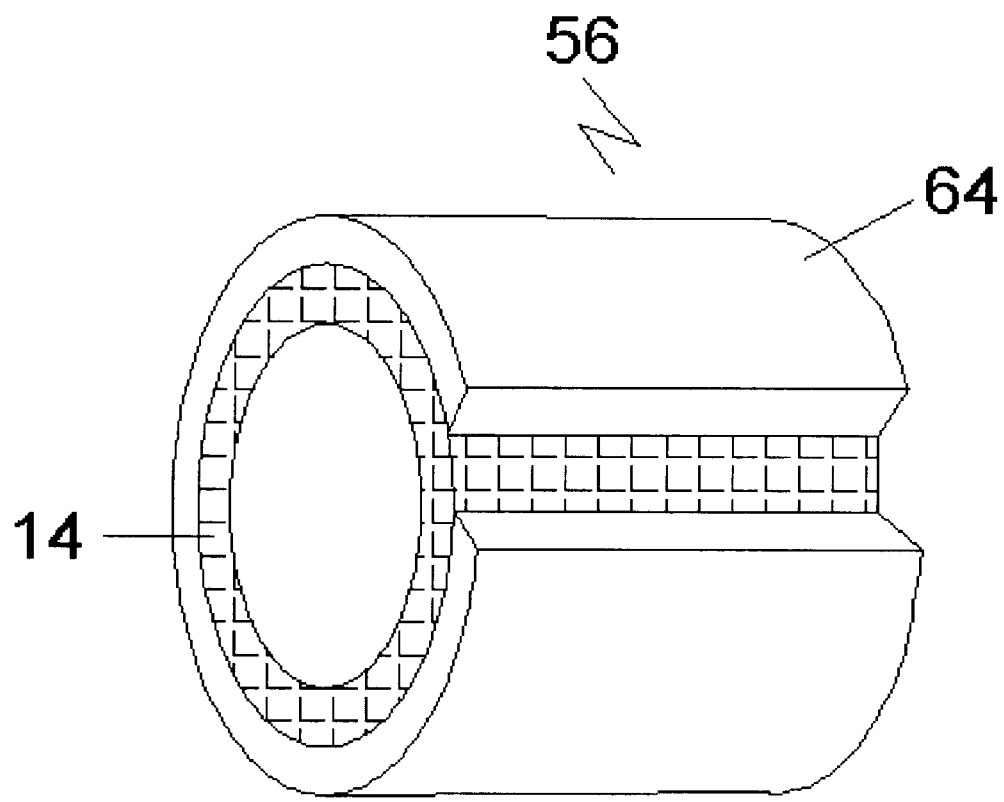
FIG. 3 is a side view of a preferred sensor cuff.
Figure 4:
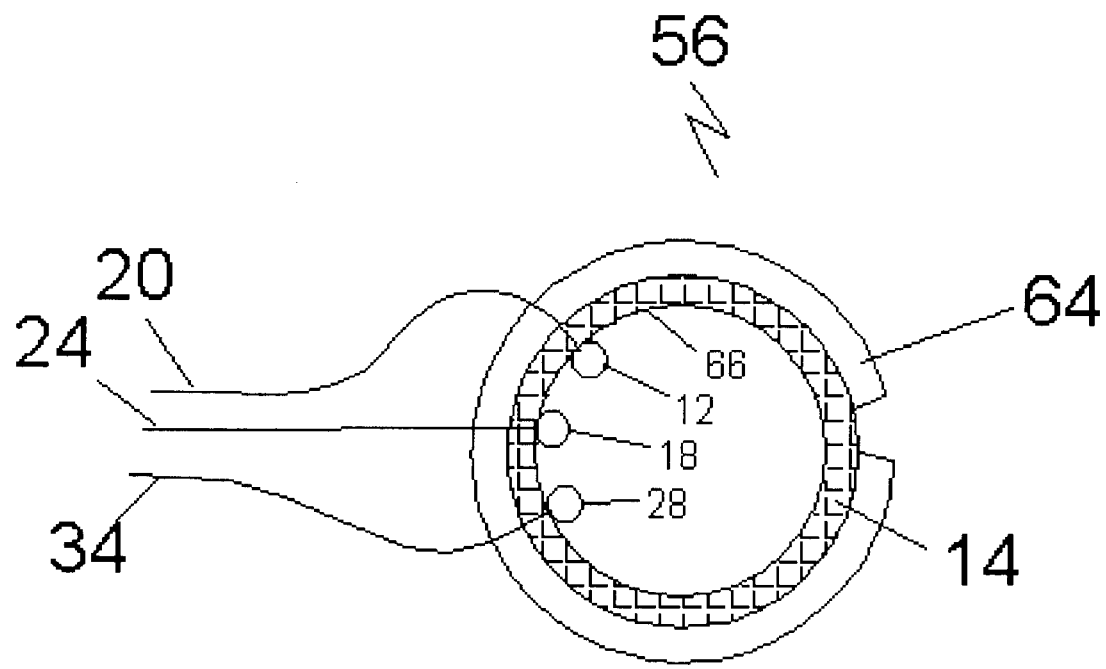
FIG. 4 is a cross-sectional view of the sensor cuff of FIG. 3.

FIG. 3 is a perspective view, and FIG. 4 is a cross sectional view, of one preferred sensor cuff 56. As is known to those skilled in the art, a cuff is a system that encircles the aorta, as a sleeve encircles the wrist. It is adapted to be placed on the aorta or attached to the aorta without surgically cutting or opening the aorta. The various sensors are designed to penetrate through the wall of the aorta so the sensing elements are disposed along the inside of the aortic wall, without protruding into the blood flow. In the embodiment depicted in FIG. 3, sensor cuff 56 is preferably comprised of a flexible material 64 which, in one embodiment, is comprised of or consists of flexible elastomeric material such as, e.g., biocompatible silicone rubber. One may use one or more of the biocompatible elastomeric materials disclosed in U.S. Pat. Nos. 5,171,281, 4,955,899 (longitudinally complaint vascular graft), U.S. Pat. No. 5,102,389 (membrane composite), U.S. Pat. Nos. 5,116,372, 6,228,060 (blood seal), U.S. Pat. No. 5,192,308 (vascular prosthesis with an elastomeric coating), U.S. Pat. No. 5,436,291 (calcification resistant biomaterials), U.S. Pat. No. 5,545,229 (functional and biocompatible intervebral disc spacer containing elastomeric material of varying hardness), and the like. The entire disclosure of each of these United States patents is hereby incorporated by reference into this specification.

Referring again to FIGS. 3 and 4, the elastomeric cuff 64 is preferably concentrically and contiguously disposed around the aortic arch 14. Lines 20, 24, and 34 extend through cuff 64 and are connected to sensors 12, 18, and 28, respectively. As is more apparent from FIG. 1, these lines 20, 24, and 34 extend from the sensors 12, 18, and 28 to the recording system 26.

In the embodiment depicted in FIGS. 3 and 4, the sensors 12, 18, and 28 are preferably located inside the wall 66 of the aortic arch 14.

FIG. 5 is a schematic of one preferred playback system 48 (see FIG. 1) which can playback some or all of the information furnished to it by recording system 44 (see FIG. 1). In particular, playback system 48 may be used to inject the various energy patterns recorded with recording system 44 into an intact healthy heart.

Referring to FIG. 5, and in the embodiment depicted, it will be seen that electrodes 68 are disposed within the baroreceptor system and used to stimulate one or more of the nerves 58, 60 (see FIG. 6) in the baroreceptor system. As known to those skilled in the art, the baroreceptor system is responsive to pressure. Reference may be had, e.g., to U.S. Pat. No. 4,791,931.

In one embodiment, the electrodes 68 stimulate at least one of the nerves in the baroreceptor system.

Figure 7:
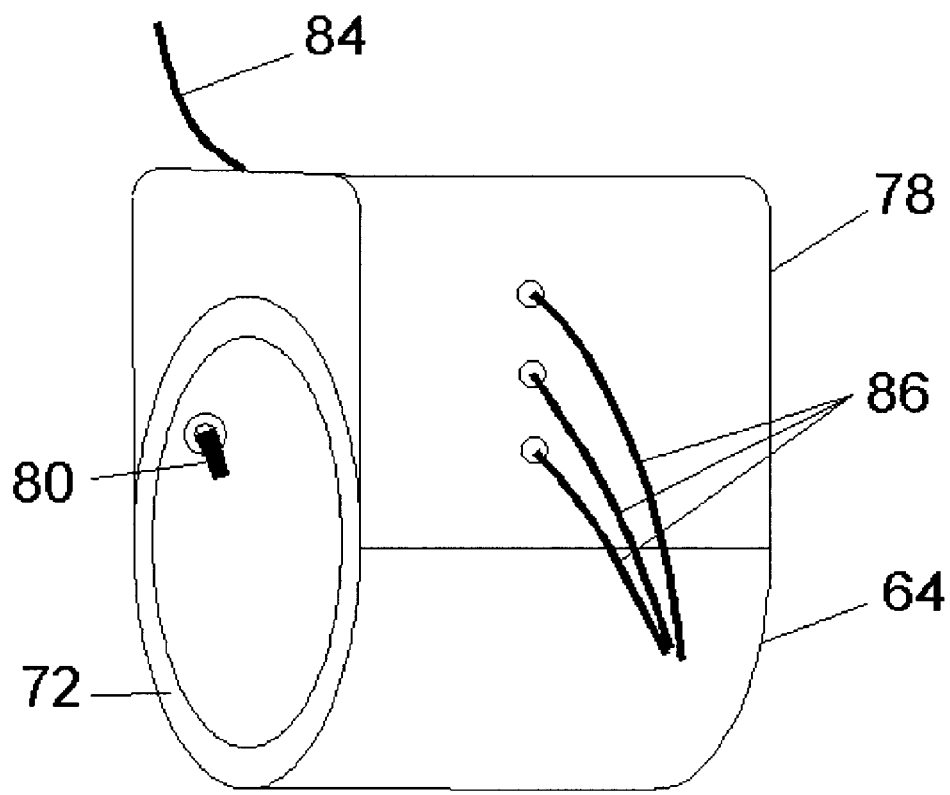
FIG. 7 is a schematic diagram of a preferred device for introducing energy pulses into the blood stream.
Figure 8:
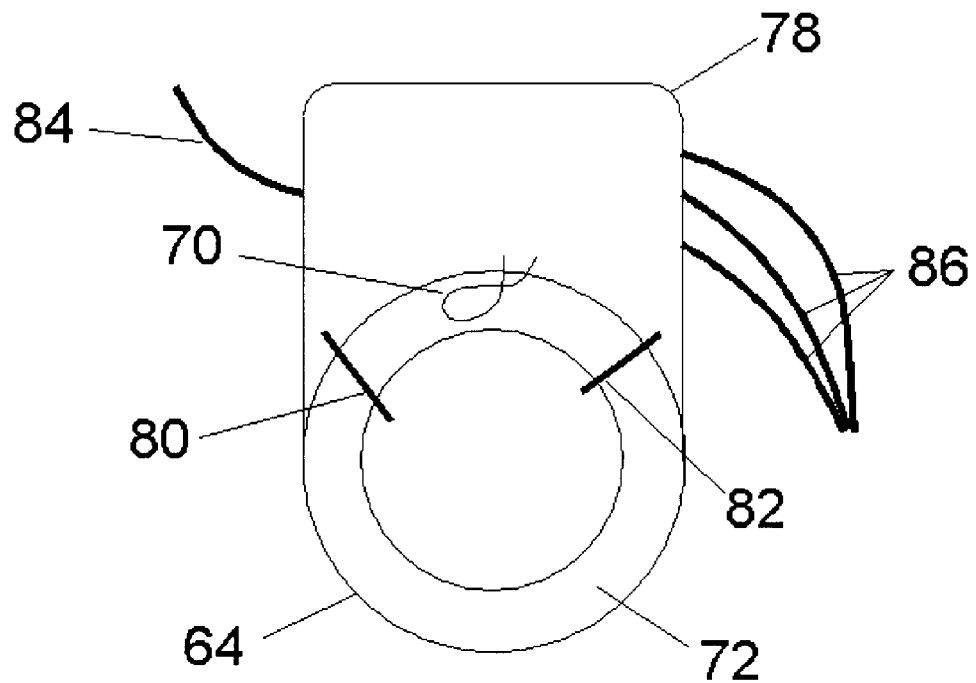
FIG. 8 an end view of the device depicted in FIG. 7.

Referring again to FIG. 5, and in one embodiment, a heat source 70 in the cylindrical implant 64 is utilized; the cylindrical implant 64 is preferably a cylinder or tube surgically sutured in series with the aorta (see FIGS. 7 and 8). The heat source 70 generates thermal pulses within the aortic arch 14.

One may use any conventional implantable heating devices such as, e.g., a resistive wire and/or the heaters disclosed in U.S. Pat. No. 6,001,090 (Thermal pharmaceutical delivery system), U.S. Pat. No. 5,133,710 (Thermal seed for treatment of tumors), and the like. The entire disclosure of each of these United States patents is hereby incorporated by reference into this specification.

Figure 6:
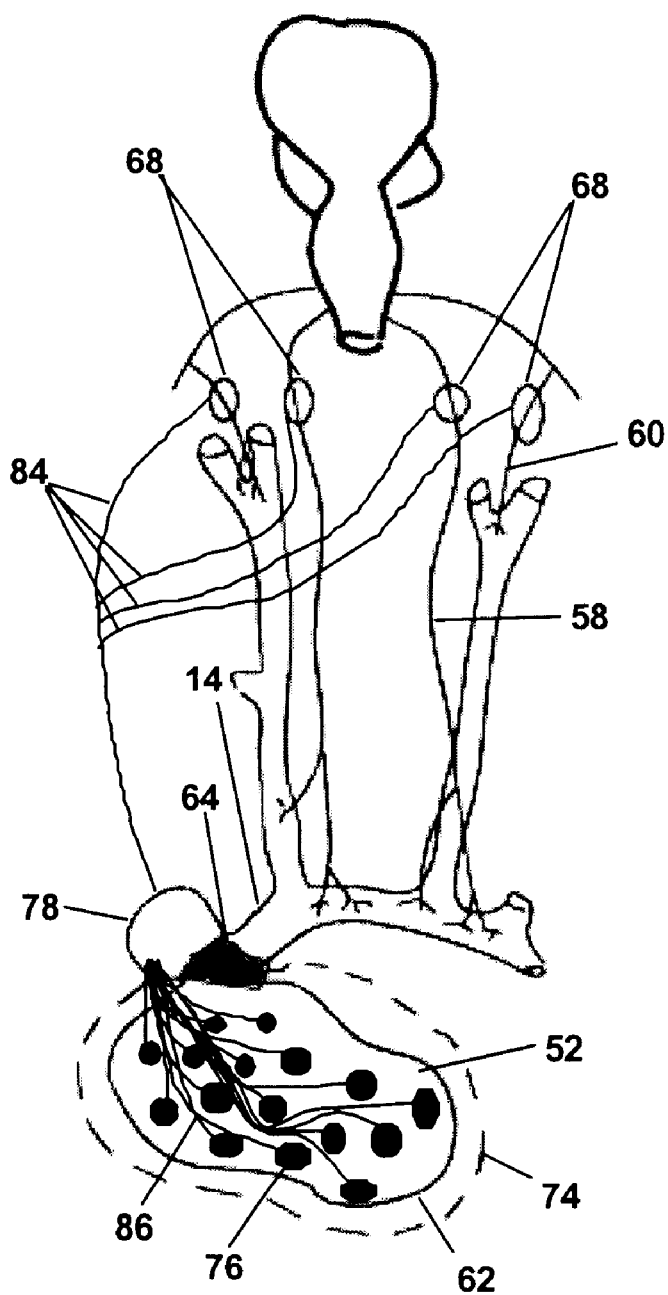
FIG. 6 illustrates the device of FIG. 5 connected to a human heart.

Referring again to FIG. 5, and in the embodiment depicted therein, an electrode array 74 distributes electrical fields over the ventricular surface 52 (see FIG. 6). In one embodiment, these electrical fields are comparable to or identical to the electrical fields recorded in recording device 44 using recording electrodes 30 (see FIG. 1). Without wishing to be bound to any particular theory, applicants believe that the reconstitution of electrical fields that are present in normal healthy hearts facilitates health.

Referring again to FIG. 5, and in the embodiment depicted therein, a sound transducer 82 extends through the wall 72 of cylindrical implant 64 (see FIGS. 7 and 8). A controller 78 times and generates electrical pulses to activate the various transducers 68, 70, 76, 82 in relation to signals from an activity sensor 80, and/or signals from a pacemaker (not shown), and/or according to a program pre-set in the controller 78 or communicated to said controller electromagnetically by remote means from outside the body (not shown) by a physician. In one embodiment, the activity sensor 80 extends through the 72 of cylindrical implant 64 (see FIGS. 7 and 8). In one embodiment, and referring to FIG. 5, one or more wires 84 extends from the controller 78 to one or more electrodes 68 on the baroreceptor afferent nerves 58 and/or 60 (see FIG. 6); and wires 86 extend from controller 78 to electrodes 76 of electrode array 74 (see FIG. 6).

FIG. 6 illustrates a preferred deployment of the heart augmentation device 48 with respect to a biological heart 62. Stimulation means (electrodes 76 of electrode array 74, heat source 70, sound source 82, e.g.) are sutured to the heart 62 and aorta 14 at appropriate incisions in each to achieve communication of the conduit with the patient's circulatory system. Cylindrical implant 64, with stimulation mean(s) 70, 82, and attached controller 78, is preferably located at the beginning of the aortic arch 14. Wires 86 from controller 78 spread over the inside of non-conducting meshwork 88 (see FIG. 9), of electrode array 74 to terminate in a plurality of electrodes 76, forming an electrode array facing away from ventricular surface 52. Additional wire 84 from controller 78 preferably connects to stimulating electrode(s) 68 on one or more afferent nerves 58 or 60 of the baroreceptor system.

FIGS. 7 and 8 are longitudinal and transverse sectional drawings detailing one embodiment of the wall 72 of cylindrical implant 64 with stimulating means 70, 82 and sensor 80 and controller 78. In this embodiment, the cylindrical implant 64 is comprised of a conduit made of elastomer or other flexible material, with controller 78 attached. Heating element 70 is embedded in the wall 72 of implant 64. Activity sensor 80 and sound producing means 82 extend from controller 78 through the wall 72 of implant 64. The wire 84 extends to one or more electrodes 68 on the baroreceptor afferent nerves 58 and/or 60, and wires 86 emerge from controller 78 extend to electrodes 76 of electrode array 74.

Figure 9:
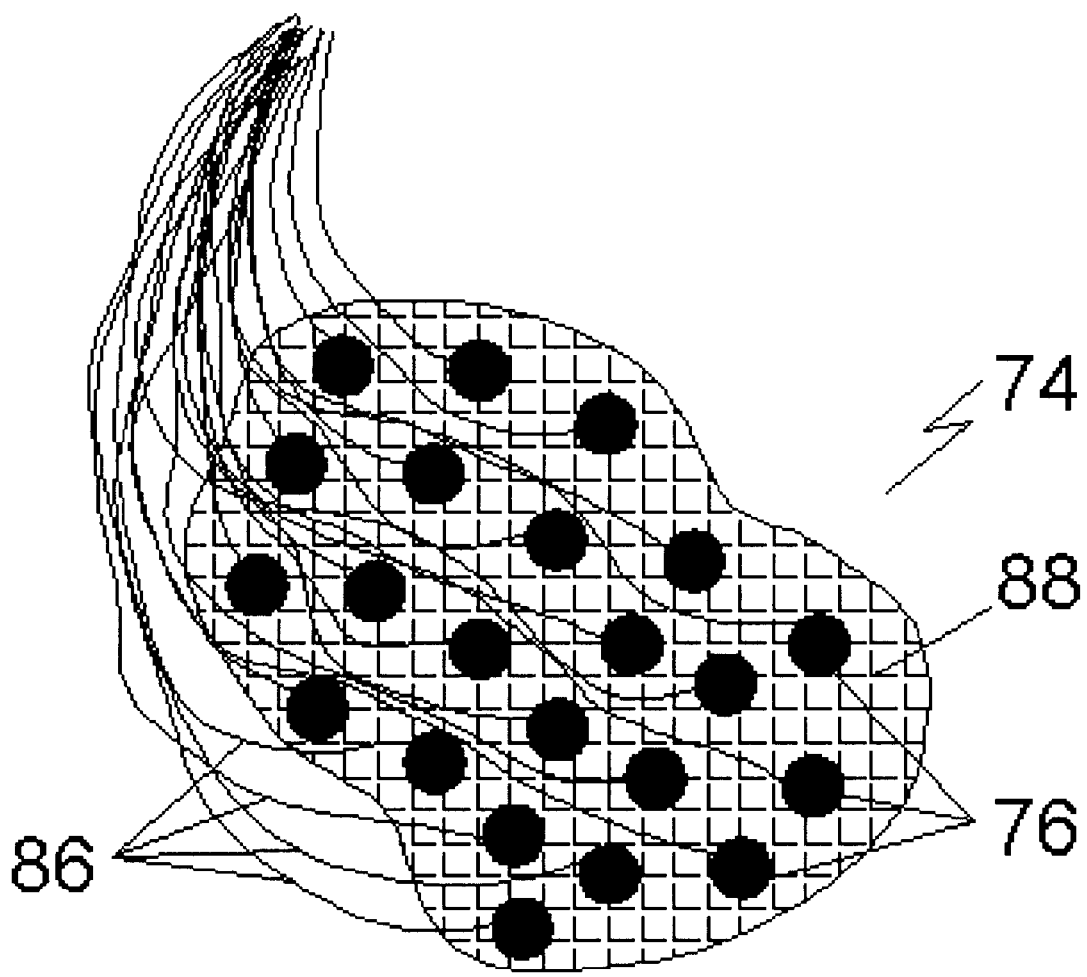
FIG. 9 schematically depicts a preferred electrode array.

FIG. 9 is a schematic of one preferred embodiment of an electrode array 74 which, in the embodiment depicted, has electrodes 76 spread over the inside of non-conducting meshwork 88 facing away from ventricular surface 52 (not shown in FIG. 9, but see FIG. 6).

Figure 10:
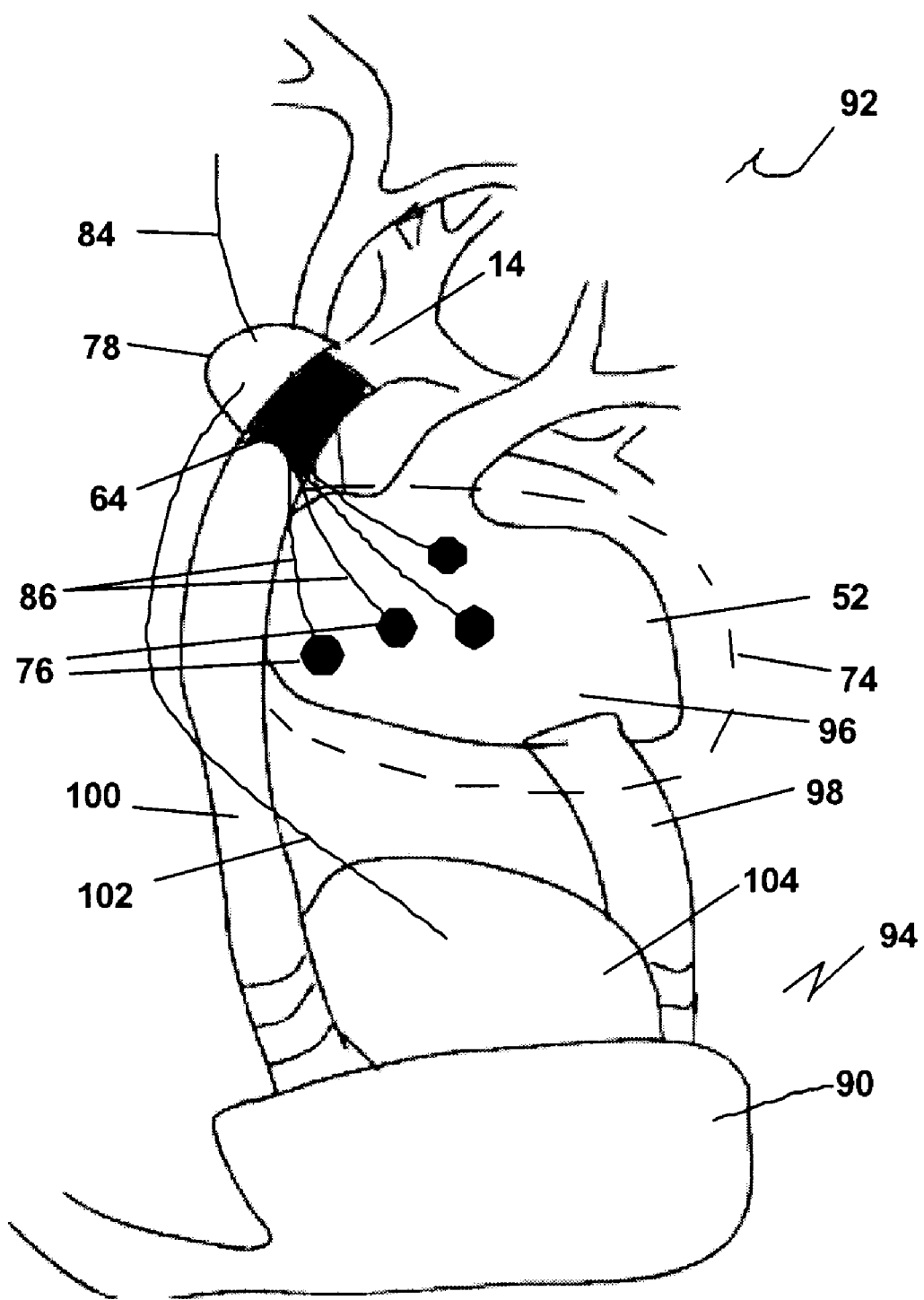
FIG. 10 illustrates the connection of this invention to an artificial heart assist pump and to a human heart.

FIG. 10 is a schematic of a preferred arrangement of a cardiac assist device 90 implanted within a patient 92 and cooperating with the assembly 48 (see FIG. 5). In one preferred embodiment, the cardiac assist device 90 is an implantable heart assist pump, such as those disclosed in U.S. Pat. No. 3,885,251 (Artificial heart pump or assist), U.S. Pat. No. 4,968,293 (Circulatory assist device), and the like; the entire disclosure of each of these United States patents is hereby incorporated by reference into this specification. Thus, e.g., the heart assist pump 90 may be a commercially available assist pumps such as, e.g., an implantable cardiac assist device such as Novacor N100 LVAS or the Baxter Healthcare device described in U.S. Pat. No. 5,810,708 ("Ventricular assist conduit with externally supported tissue valve").

Referring again to FIG. 10, and in the preferred embodiment depicted, the assist device 90 is preferably located in the preperitoneal position 94 in the left upper quadrant of the patient's abdomen (not shown). The implanted device 90 preferably provides left-sided heart support. Thus, e.g., blood is preferably withdrawn from the left ventricular apex 96 via an inflow conduit 98 and returned to the aortic arch 14 via an outflow conduit 100 communicating blood from the implanted pumping means 90 to the ascending portion of the patient's aortic arch 14. These conduits 98 and 100 are preferably attached to the natural tissues by suture rings that maintain the blood flow. Implant 64 and controller 78 are attached between tube 100 and aortic arch 14. Wires 86 extend from the controller 78 to the electrodes 76 of the electrode array 74; for the sake of simplicity of representation, only a few of the electrodes 76 are shown.

In the embodiment depicted, the electrodes 76 face away from ventricular surface 52. Additional wire 84 from controller 78 connects to one or more stimulating electrode(s) (not shown in FIG. 10, but see element(s) 68 in FIG. 6) attached to one or more afferent nerves 58, 60 (see FIG. 6) of the baroreceptor system.

In one embodiment, depicted in FIG. 10, further additional lines 102 connect between timing means (not specifically shown) in assist device controller 104 to controller 78. In one aspect of this embodiment, the connection between the artificial heart outflow conduits 98/100 and the devices 48/64 of the present invention is made with a polarized coupling means (not shown) that prevents incorrect assembly of the system, as is disclosed in U.S. Pat. No. 5,810,708 (Ventricular assist conduit with externally supported tissue valve). The entire disclosure of this United States patent is hereby incorporated by reference into this specification.

Figure 11:
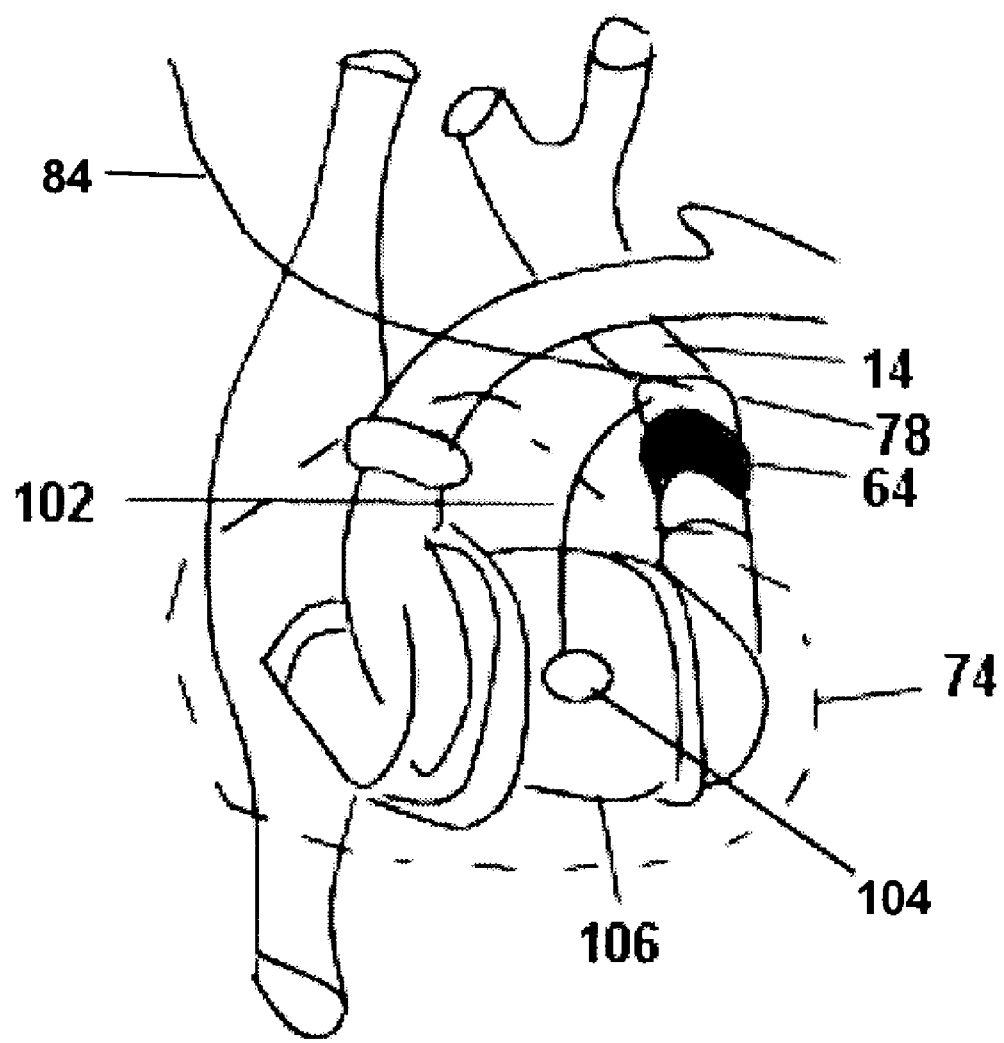
FIG. 11 illustrates the connection of this invention to an artificial heart.

FIG. 11 is a schematic representation of an arrangement in which a completely implantable replacement artificial heart 106 is used. These artificial hearts are well known to those skilled in the art; reference may be had, e.g., to U.S. Pat. No. 5,751,125 (Artificial heart with sensorless motor), U.S. Pat. No. 5,947,892 (Rotary blood pump), U.S. Pat. No. 5,300,111 (Total artificial heart), U.S. Pat. No. 4,976,729 (Elliptical artificial heart), and the like. The entire disclosure of each of these United States patents is hereby incorporated by reference into this specification.

Referring again to FIG. 11, and in the embodiment depicted, artificial heart 106 pumps blood into and out of aorta 14. Implantable cylindrical device 64 and controller 78 are attached between artificial heart 106 and aortic arch 14. Wires from controller 78 (not shown in FIG. 11, but see element 86 of FIG. 6) preferably spread over the inside of non-conducting meshwork 88 (see FIG. 9) to terminate in a plurality of electrodes 76 (see FIGS. 66 and 9), thereby forming an electrode array 74 facing away from the surface of artificial heart 106. Additional wire 84 from controller 78 connects to stimulating electrode(s) (not shown, but see electrodes 68 in FIG. 6) on one or more efferent nerves 58, 60 of the baroreceptor system. Further additional wire 102 connects controller 78 with artificial heart controller 104. The connection between the artificial heart outflow conduit and the present invention is, in one embodiment, made with a polarized coupling means that prevents incorrect assembly of the system, as disclosed in U.S. Pat. No. 5,810,708 (Ventricular assist conduit with externally supported tissue valve). The entire disclosure of this United States patent is hereby incorporated by reference into this specification.

FIG. 12 is a schematic representation of a valvular connector 108 that can be added to the wall 72 of implanted cylindrical device 64 in order to convert nonpulsatile flow to pulsatile flow. The human heart is a cyclic or rhythmic pump by virtue of the operation of its four muscular chambers which alternatively relax to allow filling and then contraction, producing a pulse or throb or forceful ejection of blood that then flows through the arterial system with a pressure wave and thus giving rise to pulsatile flow.

Figure 12A:
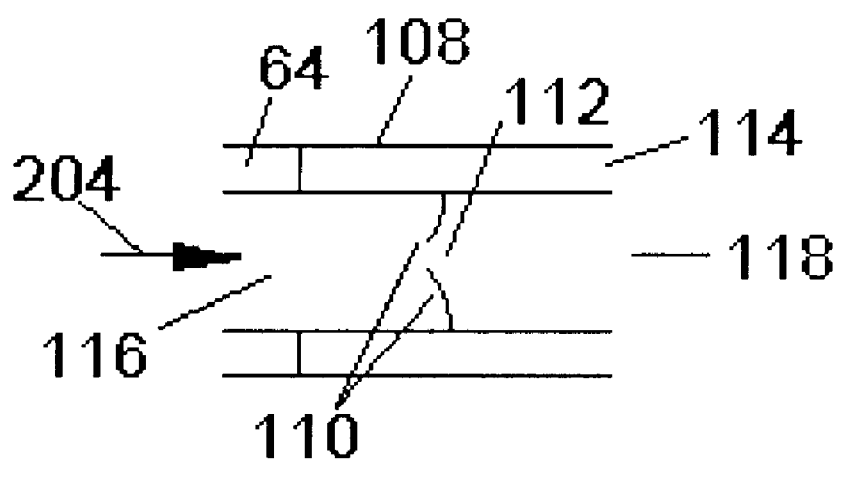
FIGS. 12A, 12B, and 12C each are partial schematic views of a valve device for conversion of nonpulsatile flow to pulsatile flow.
Figure 12B:
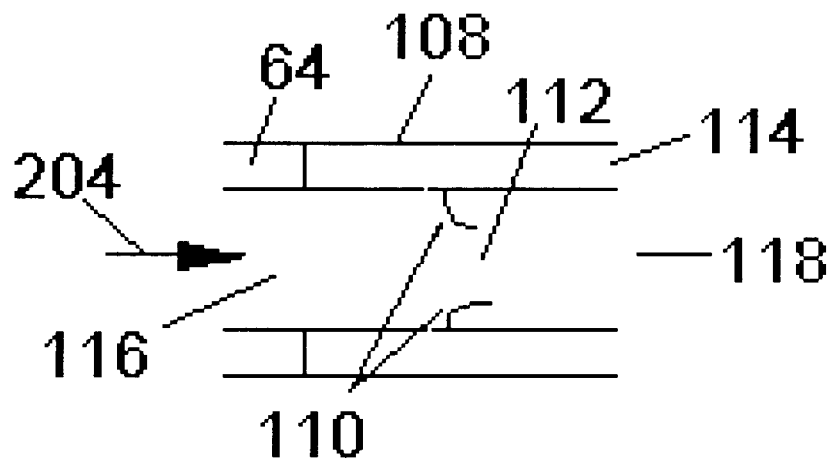
Figure 12C:
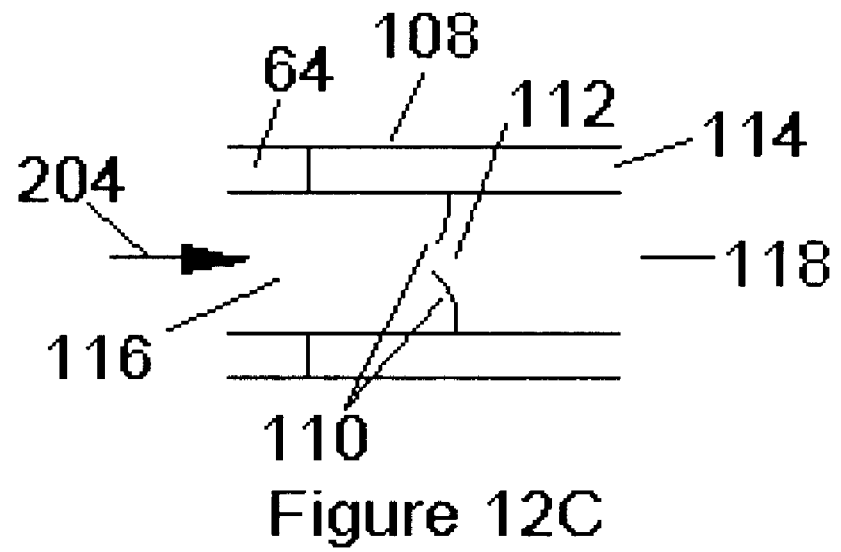

Referring to FIG. 12A, within the valved conduit 108 is disposed a flexible diaphragm 110 with a central opening 112 so adapted that it maintains its geometry and restrains blood flow up to a certain level of pressure which, in one embodiment, is about 120 millimeters of mercury and which approximates the systolic pressure. When the specified pressure level is exceeded, the valved conduit 108 pops open valve 110 (see FIG. 12B), thereby allowing dissipation of built up pressure and acting as an implantable pressure relief valve. Thereafter, when the pressure drops to a specified lower value (such as, e.g, 80 millimeters of mercury, approximating the disastolic pressure), the valve 110 closes (See FIG. 12C) and the diaphragm is restored to it's initial condition to repeat the pulsatile cycle.

The diaphragm 110 is preferably fashioned from a resilient material such as, e.g., porcine xenograft material or from a sheet of either animal or human tissue. Reference may be had, e.g., to U.S. Pat. No. 5,843,180 (Method of treating a mammal having a defective heart valve), U.S. Pat. No. 4,731,074 (Heart valve prosthesis, method for producing a heart valve prosthesis and mould applied thereby), and the like. The entire disclosure of each of these United States patents is hereby incorporated by reference into this specification.

In one embodiment, the diaphragm 110 is inserted into and disposed within grooves (not shown) in the wall 114 of the connector 108, and can be replaced, if necessary, using catheter-based endovascular procedures. Reference may be had, e.g., to U.S. patent application Ser. No. 20010002445; the entire disclosure of this United States patent application is hereby incorporated by reference into this specification.

The valvular connector 108 preferably has an inflow end 116 and an outflow end 118, and the connections to this connector are preferably made with a polarized coupling means that prevents incorrect assembly of the system, as disclosed in U.S. Pat. No. 5,810,708 (Ventricular assist conduit with externally supported tissue valve). The valvular connector 108 is connected to the implant 64.

Figure 13:
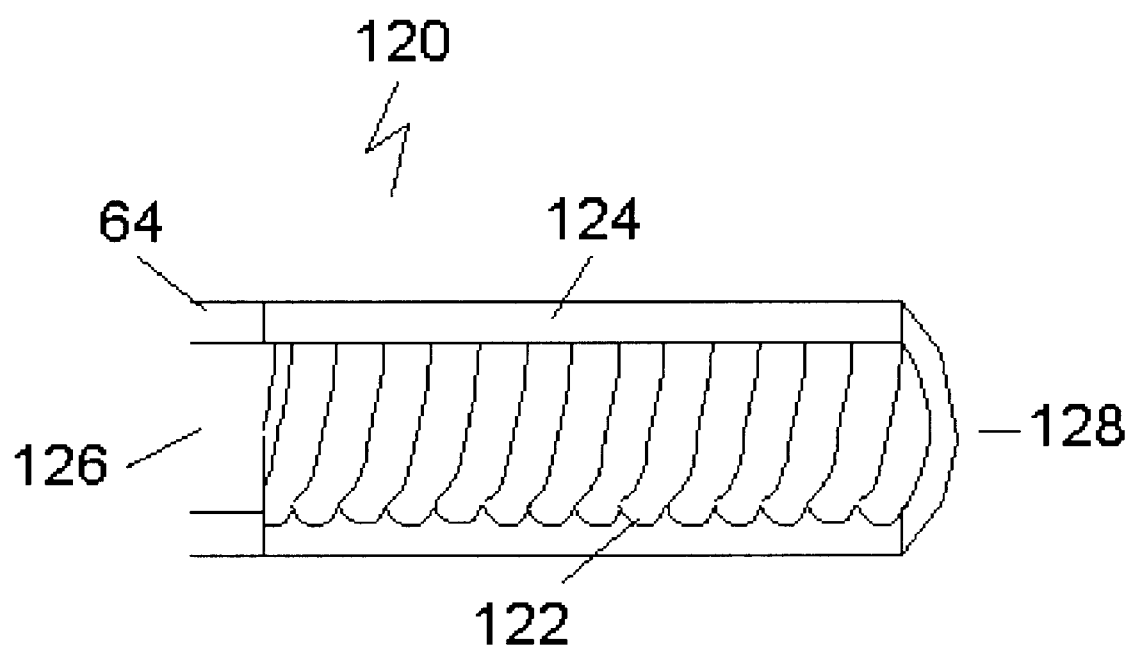
FIG. 13 is a partial schematic view of a device for imparting spiral motion to flowing blood.

FIG. 13 is a schematic representation of a connector 120 that can be attached to the implant 64 when it is used with cardiac assist devices and artificial hearts that do not produce a vortical flow. Helical grooves 122 cut into the wall 124 of the attachment 120 impart spiraling motion to blood flowing through device 120. It is believed that vigorous blood-flow vortices contribute to valve action and ensure that the blood-exposed surfaces of the conduit or arteries are scrubbed by the flowing blood, thereby avoiding blood stagnation, stasis, and the formation of clots that can be sloughted off as dangerous emboli.

Referring to FIG. 13, and in the preferred embodiment depicted therein, it will be apparent that the helical grooves 122 are disposed on the interior wall of device 120 and cause blood flowing through said device to engage in helical flow. One may use the device of FIG. 13 to achieve such helical flow. Alternatively, or additionally, one may use one or more of the prior art devices adapted for such purpose.

Thus, by way of illustration and not limitation, one may use the device disclosed in U.S. Pat. No. 5,628,909, the entire disclosure of which is hereby incorporated by reference into this specification. This patent claims, in part, a filter comprising a tubular, substantially cylindrical, porous membrane mounted coaxially with and radially spaced from a generally cylindrical profiled surface, which surface is formed with at least one helical groove such that a fluid to be filtered is passed into the filter from one end thereof between the membrane and the profiled surface in a helical flow, and means for inducing or enhancing, in the helical flow of the fluid to be filtered, a corkscrew vortex flow, said means comprising the shape of said groove, when seen in longitudinal cross section, being concave and formed of a substantially continuously curved surface.

Alternatively, or additionally, one may use other means of inducing helical flow. Reference may be had, e.g., to U.S. Pat. No. 4,107,048 (turbulence amplifier baffle), U.S. Pat. Nos. 4,739,634, 6,213,633, 4,634,434, 5,590,240 (water heater with coaxial helical flow paths), U.S. Pat. Nos. 4,047,433, 3,844,888 (helical flow deflector), U.S. Pat. No. 5,899,673 (helical flow compressor), and the like. The entire disclosure of each of these United States patents is hereby incorporated by reference into this specification.

Referring again to FIG. 13, and the in embodiment depicted therein, in one aspect of such embodiment the grooves 122 are geometrically optimized utilizing advanced computational fluid mechanics to yield high hydrodynamic efficiency and vortical flow patterns matching as closely as possible those measured in the intact aortic arch, and to avoid any areas of flow separation. Grooves 122 are preferably highly polished to remain free of thrombus accumulation. The embodiment depicted FIG. 13 has an inflow end 126 and an outflow end 128, and the connections to implant 64 are preferably made with a polarized coupling means that prevents incorrect assembly of the system, as disclosed in U.S. Pat. No. 5,810,708 (Ventricular assist conduit with externally supported tissue valve).

Figure 14:
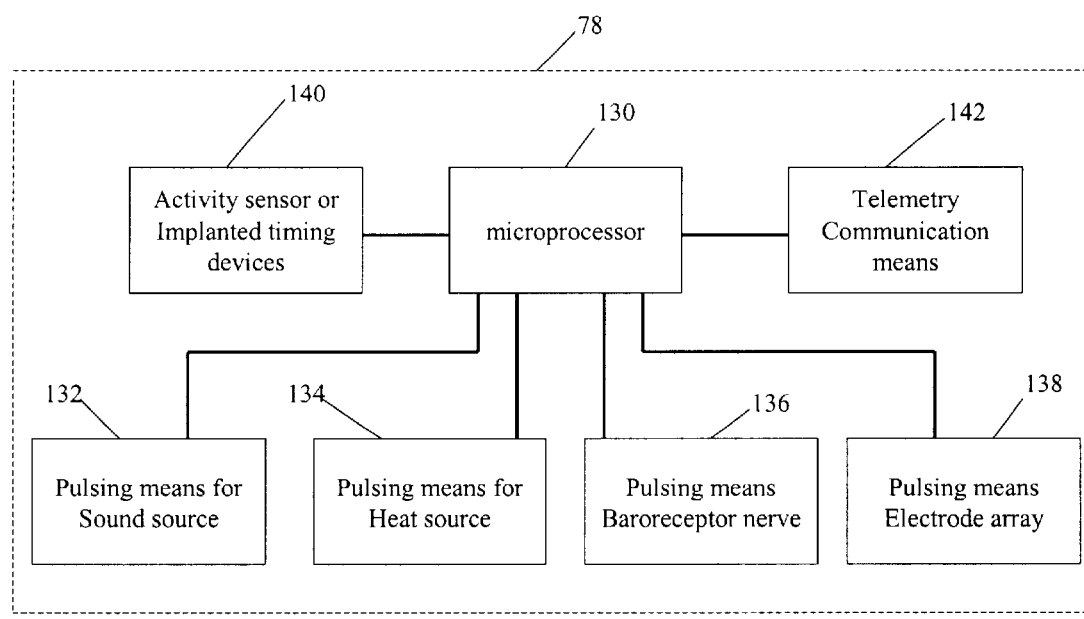
FIG. 14 is the schematic diagram of a preferred controller's elements.

FIG. 14 is a schematic representation of one preferred controller 78. In this embodiment, the microprocessor 130 integrates functioning and timing of various pulsing means 132–138 in accordance with a pre-programmed internal algorithm or in accordance with data received from activity sensor or implanted timing device in cardiac assist device or artificial heart, or in accordance with a pacemaker (not shown). The activity of sensor 140 modifies the outputs to said pulsing means 132–138 as appropriate or modifies outputs on the basis of information from externally applied signals provided by communication means 142. The microprocessor 130 operates to optimize the relationships between the frequencies and amplitudes and phase shifts between the various rhythms established by or enhanced by the various pulsing means, allowing for changes in the algorithm as new information on this subject becomes available from research or in relation to signals provided by a physician. Telemetry communication means 142 allows outputs of processor 130 or timing algorithms to be adjusted by remote data storage system or phone system devices so that a physician can interact remotely with the invention to optimize the timing, amplitudes, and phase relations of pulses delivered by the various pulsing means. Pulsing means for sound source 132 connect to sound source 82; pulsing means for heat source 134 connects to heat source 70; pulsing means 136 connects to the electrodes 68 on the baroreceptor nerve 58, 60; and pulsing means 138 connects to the electrodes 76 on the ventricular surface 52 (see FIGS. 6, 10, and 11).

It is to be understood that the aforementioned description is illustrative only and that changes can be made in the apparatus, in the ingredients and their proportions, and in the sequence of combinations and process steps, as well as in other aspects of the invention discussed herein, without departing from the scope of the invention as defined in the following claims.

We claim:

1. An implantable apparatus for treating a heart of a living organism, wherein said implantable apparatus is comprised of means for withdrawing blood from said heart, means for imparting helical flow to said blood, means for recording at least one energy characteristic of said heart, and means for imparting energy to said living organism, wherein:
   (a) said energy characteristics are selected from the group consisting of the characteristic thermal energy of said heart, the characteristic acoustic energy of said heart, the characteristic electromagnetic energy of said heart, the characteristic magnetic energy of said heart, the characteristic pulsatile energy of said heart, and mixtures thereof, and
   (b) said energy imparted to said living organism is selected from the group consisting of thermal energy, acoustic energy, electromagnetic energy, magnetic energy, pulsatile energy and mixtures thereof.

2. The implantable apparatus as recited in claim 1, wherein said implantable apparatus further comprises a heart assist device.

3. The implantable apparatus as recited in claim 1, wherein said implantable apparatus further comprises an artificial heart.

4. The implantable apparatus as recited in claim 1, wherein said means for recording at least one energy characteristic of said heart is comprised of telemetry means.

5. The implantable apparatus as recited in claim 4, wherein said telemetry means is comprised of an implanted transceiver.

6. The implantable apparatus as recited in claim 5, wherein said implantable apparatus further comprises an external receiver.

7. The implantable apparatus as recited in claim 6, wherein said external receiver is an external transceiver.

8. The implantable apparatus as recited in claim 7, wherein said external transceiver is operatively connected to an external controller.

9. The implantable apparatus as recited in claim 8, wherein said implanted transceiver is operatively connected to an implanted controller.

10. The implantable apparatus as recited in claim 9, wherein said characteristic energy of said heart is substantially identical to said energy imparted to said living organism.

11. The implantable apparatus as recited in claim 9, wherein the characteristic acoustic energy of said heart is imparted to said living organism.

12. The implantable apparatus as recited in claim 9, wherein the characteristic photonic energy of said heart is imparted to said living organism.

13. The implantable apparatus as recited in claim 9, wherein the characteristic thermal energy of said heart is imparted to said living organism.

14. The implantable apparatus as recited in claim 9, wherein the characteristic electrical energy of said heart is imparted to said living organism.

15. The implantable apparatus as recited in claim 9, wherein the characteristic magnetic energy of said heart is imparted to said living organism.

16. The implantable apparatus as recited in claim 1, further comprising means for recreating said characteristic energy of said heart.

17. The implantable apparatus as recited in claim 16, wherein said means for recreating said characteristic energy of said heart is comprised of telemetry means.

18. The implantable apparatus as recited in claim 16, wherein said means for recreating said characteristic energy of said heart is comprised of means for sensing the beating of said heart.

19. The implantable apparatus as recited in claim 16, wherein said means for recreating said characteristic energy of said heart is comprised of means for synchronizing the beating of said heart with said means for imparting energy to said blood.

20. The implantable apparatus as recited in claim 1, wherein said means for delivering energy to said blood is comprised of a programmable computer.

* * * * *